Jan. 16, 1973 H. A. LUCERNE Plant Pat. 3,292
LEMON-LIME TREE
Filed June 16, 1971 2 Sheets-Sheet 1
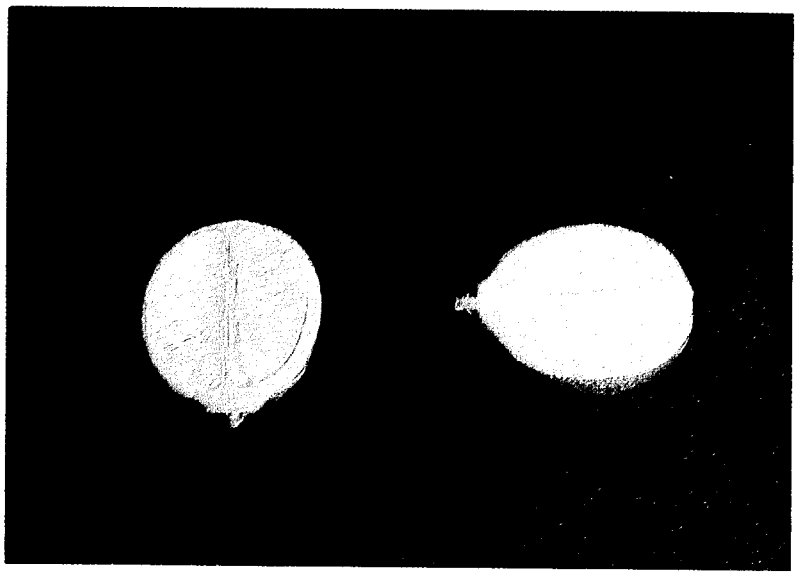
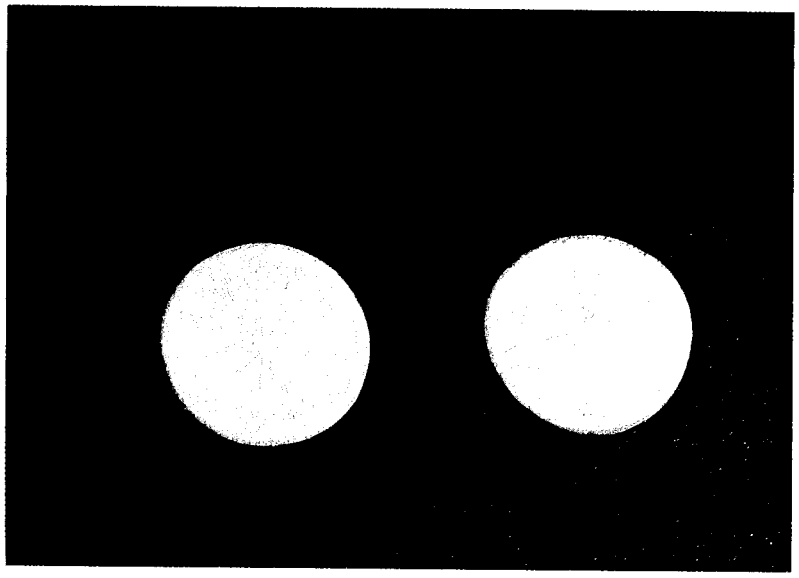
INVENTOR
HERMAN A. LUCERNE
Smith, Michael, Bradford & Gardiner
ATTORNEYS Jan. 16, 1973 H. A. LUCERNE Plant Pat. 3,292
LEMON-LIME TREE
Filed June 16, 1971 2 Sheets-Sheet 2
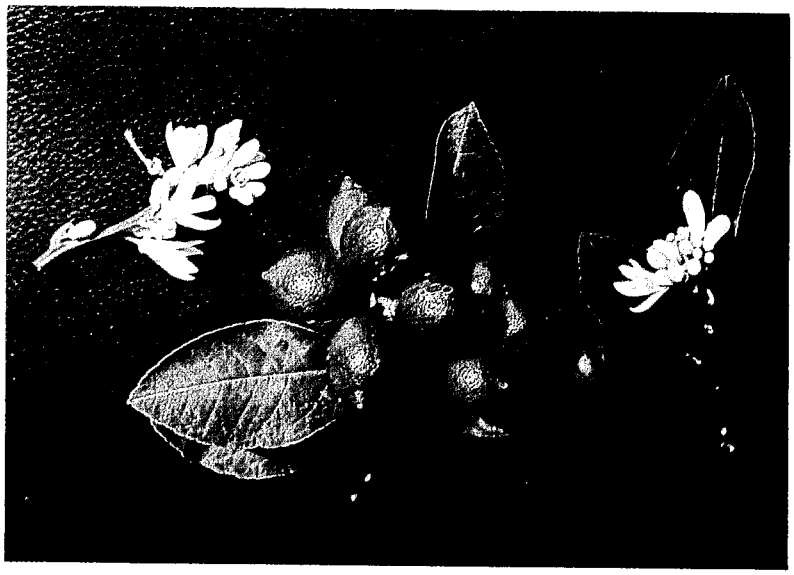
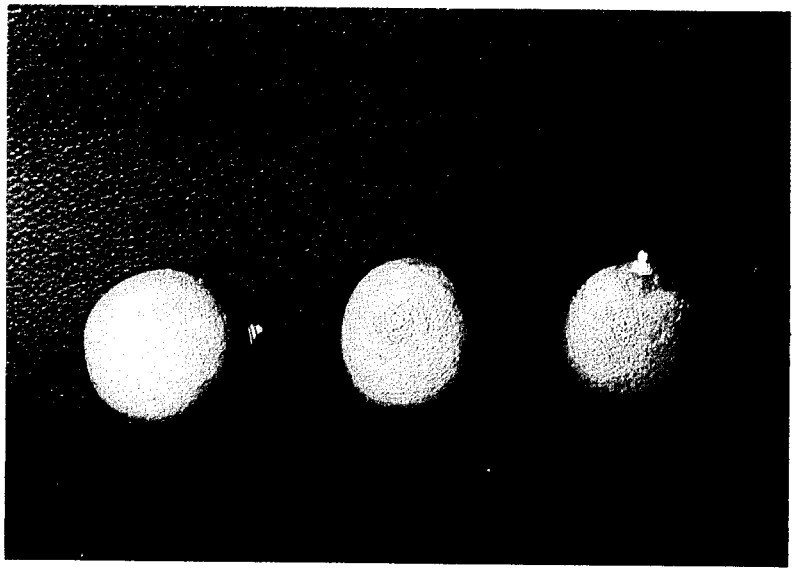
INVENTOR
HERMAN A. LUCERNE
Smith, Michael, Bradford & Gardiner
ATTORNEYS

United States Patent Office

Plant Pat. 3,292
Patented Jan. 16, 1973

3,292

LEMON-LIME TREE

Herman Arthur Lucerne, 633 SW. 2nd St.,
Florida City, Fla. 33030

Filed June 16, 1971, Ser. No. 153,905
Int. Cl. A01h *5/03*
U.S. Cl. Plt.—45 1 Claim

ABSTRACT OF THE DISCLOSURE

A lemon-lime combination resembling most closely the Perrine lemon (*Citrus aurantifolia* c. Mexican ♀ × Citrus limon c. Genoa ♂) but bearing fruit distinguished therefrom by a calyx end evenly rounded, sometimes slightly ribbed and furrowed, rarely slightly necked, a stylar end evenly rounded, very faintly nippled, and with a deciduous style, and often producing seedless fruit.

BACKGROUND

This invention relates to a new and distinct variety of citrus tree and its fruits, which possess many characteristics of both the Tahiti lime and the lemon. This variety was discovered by me as a fruiting tree in a planted row of a lime grove on my property located near Homestead, Dade County, Fla. The trees of this grove originated in my nursery, where this invention is believed to have occurred as a chance natural hybrid, the seed source being rough lemon and the pollen source probably a lime. It is surmised that the budded variety failed to survive, and that the hybrid was permitted to grow and was transplanted to the grove at a growth stage at which distinguishing characteristics were not evident to the field crew. The tree has retained its identity through vegetative propagation which I have accomplished by air layering and by budding on such commonly employed rootstocks as seedlings of the Rough Lemon.

RELATED PAPERS

This invention is the subject matter of Disclosure Document No. 4,331 filed in the United States Patent Office on Feb. 23, 1971.

TECHNICAL DESCRIPTION

Tree

General characteristics: The tree is small, spreading, evergreen, vigorous, productive, rather compact, similar in rate of growth, habit, and general appearance to trees of Tahiti lime.

Leaves are alternate, unifoliate, with a distinct articulation between the petiole and the leaf blade. Petioles short, from 5/16 to 23/32 of an inch long, averaging 7/16 of an inch, margined or very narrowly winged; if winged, the wings are 3/32 of an inch or less in width, leaf blades commonly oval to elliptic-oval, rarely obovate or oblanceolate; base of the blade obtuse, tips usually acuminate, rarely retuse or emarginate. Margin of the blade finely serrulate, serrations irregular, shallow. Blades from 2 and 1/16 to 4 and 3/32 inch; averaging 3 and 3/8 inch long; the width varying between 1 and 7/32 inch and 2 and 3/16 inch; averaging 1 and 23/32 inch at the broadest portion of the blade. Leaf blades longer on suckers or watersprouts, to 4 and 29/32 inch or more long and 2 and 11/32 inch or more broad. Oil glands in the blade numerous, inconspicuous, tiny, only apparent as minute pelucid dots when the blade is held up to the light; the oil has an aroma reminiscent of grapefruit. Leaf midrib conspicuous above, slightly prominent below; lateral veins inconspicious above, not prominent below. Leaf blades glaucous, thin, uniformly dark green above, lighter green beneath.

Thorns few or absent on new growth originating on the older mature portions of the crown of the tree; solitary, sharp-pointed, slender axillary thorns are present on juvenile growth, averaging 3/16 of an inch in length and 3/64 of an inch or less in diameter at the base. Axillary thorns on watersprouts or suckers much larger, stout, sharp-pointed, averaging 25/32 of an inch long.

Flowers mostly bisexual, occasionally male because of abortion of the pistil; either solitary in the leaf axils or borne in few-flowered symose auxiliary or terminal racemes. Flower buds medium-size, averaging 25/32 of an inch in overall length in aestivation, pinkish-purple in color. Pedicels short, about 13/32 of an inch long. Sepals 4 or 5, fused, forming a small cup-like calyx 1/8 to 5/32 of an inch deep and 3/16 to 9/32 of an inch in diameter; both pedical and calyx light green in color, partially or wholly flushed with reddish-purple. Tips of the calyx lobes blunt but strongly mucronate. Petals 4 or 5, strap-shaped, the tips obtuse, acute, or acuminate; not clawed at the base imbricate in the bud, averaging 25/32 of an inch long and 9/32 of an inch wide, adaxial (upper) surface white, abaxial surface reddish-purple. Stamens 5 or 6 times as many as petals, polyadelphous, with the filaments cohering along a part or along most of their length into a few bundles; stamens inserted beneath the disk. Filaments white, anthers bright yellow, pollen abundant, bright yellow in color. The disk is small, green, cup-shaped, enclosing the base of the ovary. Pistil small, average length 1/2 inch; ovary globose, 1/8 to 5/32 of an inch high, somewhat tapered at the top but clearly delineated from the deciduous style, cream or light green in color. Style cylindrical, average length 9/32 of an inch, cream-colored. Stigma capitate, nearly as large as the ovary, bright yellow (the same color as the mothers). Fragrance sweet, pleasing, suggestive of orange blossoms.

Flowering and fruiting habit: Under the natural conditions of south Florida, similar to and more or less coinciding with the flowering and fruiting habit of the Tahiti lime. The principal flowering season is late spring, but some fruits are produced intermittently throughout the year, and the tree often has ripe fruits, fruits in various stages of development, and newly-opened flowers all at the same time. The yield per tree is similar to or a little greater than the yield from Tahiti lime trees of approximately the same age when grown under comparable environmental conditions. The fruits, like most of the lime, develop juice while still green and immature.

Fruit

*External fruit characters*

Mature fruit color: The fruit reaches maturity (i.e. full size, juiciness, and with fully formed and mature seeds) while still a uniform dark green color when borne singly along the branch; when clustered in racemes, the color is uniformly dark green on exposed surfaces, but with a yellow or yellow-green spot where the surface of one fruit rests against that of another fruit. Within a few days after picking, the fruit cures to a uniform lemon yellow color. If fruit is permitted to remain on the tree after becoming full-sized, such fruit also eventually turn a uniform lemon yellow.

Surface of the fruit medium smooth, with slight depressions over the largest oil glands; surface faintly ribbed, glossy.

Shape round to obovate or oval, symmetrical.

Size medium, diameter 1 and 3/4 to 2 and 1/4 inch, height from 2 and 1/8 to 3 and 1/16 inch.

Base evenly rounded, sometimes slightly ribbed and furrowed, rarely slightly necked.

Calyx even, small, irregularly divided, divisions short, lobes blunt, thin; tips persistent, mucronate.

Stem small, 1/8 of an inch or less in diameter.

Apex evenly rounded, very faintly nippled.

Aerole inconspicuous, irregular, slightly sunken, indistinct; aerolar area narrow, average diameter 15/32 of an inch, very slightly elevated around the stylar scar, with faint radial ribs; oil glands inconspicuous.

Style deciduous; stylar scar small, 3/32 of an inch or less in diameter, even or faintly protruded; if protruded, less than 3/128 of an inch so.

*Internal fruit characters*

Rind thin, 9/64 to 3/16 of an inch, averaging 5/32 of an inch in medium cross-section, firm adherence medium-strong, puffiness none.

Oil glands numerous, small, inconspicuous, about 412 in number per square inch or surface; the primary glands (vertical to the surface) globose to abovoid in shape, small, average diameter paralleled to the surface 3/64 of an inch; surface slightly depressed, contour between primary glands even.

Oil not abundant, highly volatile when released, aroma strong and rank when the oil is first released, with lime and orange tones; aroma quickly fades to a mild grapefruit-like odor on evaporation.

Glandular layer thin, comprising from 25 to 33 percent of the thickness of the rind, green in color, curing to yellow.

Mesocarp (albedo) thin, white, vascular bundles inconspicuous, texture medium-soft.

Axis in medium cross-section round to oval, small, solid, white, average mid-diameter 1/4 of an inch, average basal diameter 5/32 of an inch, average apical diameter 3/16 of an inch.

Segments from 10 to 12, mainly 10 or 11, adherence medium-strong, little rag from rind, septa thin, relatively tough, dorsal contour convex.

Pulp uniformly light golden yellow in color, fine-grained and tender in texture, vesicles small and slender, juicy.

Juice strongly acid, bitterness slight or none, aroma weak and indefinite. Flavor mostly sour, with faint indefinite overtones, no after taste. Analysis of the juice of fully mature yellow-skinned fruits shows an average acid content of 4.9 percent, and BRIX of 8.6 percent.

Perfect seeds from none to 10 per fruit, medium sized, plump, average length 13/32 of an inch, average width 9/32 of an inch, ovate, slightly angular at the placental end; surface smooth, strongly veined; outer seed coat cream-colored, translucent; inner seed coat varying in color from light brown to reddish purplish. Chalazal spot dark purplish. Cotyledons light green, color more intense on their adaxial surfaces.

Imperfect seeds from none to 10 or more, mostly very small, less than 3/16 of an inch long, brownish; occassionally as long as perfect seeds and similarly colored, but flattened.

Degree of seediness varies from one crop to another; some sets of fruit are mostly seedy, whereas other sets are largely seedless.

Of all other lemon-lime combinations of which I am aware, my tree produces fruit which more nearly resembly those of the Perrine lemon (*Citrus aurantifolia* ♀×*Citrus limon* c. Genoa ♂, described and figured by Walter T. Swingle, T. B. Robinson, and E. M. Savage in New Citrus Hybrids. United States Department of Agriculture Circulat 181, 1931) than of any other lemon-lime combination, but the fruits of my tree differ from those of the Perrine lemon in the following morphological characteristics:

The calyx end of the fruits of my tree are evenly rounded, sometimes slightly ribbed and furrowed, rarely necked, whereas the Calyx end of the Perrine lemon is decidedly necked, with abrupt protuberances surrounding the calyx;

The stylar end of the fruits of my tree are evenly rounded, very faintly nippled, and with a deciduous style, whereas the stylar end of the fruits of Perrine lemon ends in a small nipple characteristic of lemon fruits, and the style and stigma are often persistent on the nature fruit;

My tree often produces seedless fruits, whereas those of the Perrine lemon always have seeds.

I claim:

1. A new and distinct variety of lemon-lime tree substantially as herein shown and described, characterized particularly as to novelty by fruit having a calyx end evenly rounded, sometimes slightly ribbed and furrowed, rarely slightly necked, a stylar end evenly rounded, very faintly nippled and with a deciduous style, often producing seedless fruit.

No references cited.

ROBERT E. BAGWILL, Primary Examiner